Figure 1:
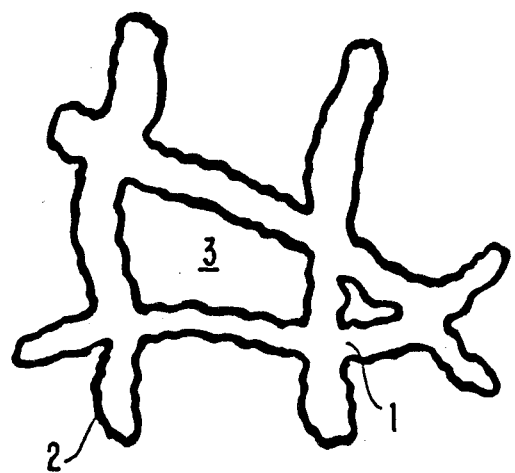

United States Patent [19]

Juda et al.

[11] Patent Number: 4,614,575
[45] Date of Patent: Sep. 30, 1986

[54] POLYMERIC HYDROGEL-CONTAINING GAS DIFFUSION ELECTRODES AND METHODS OF USING THE SAME IN ELECTROCHEMICAL SYSTEMS

[75] Inventors: Walter Juda, Lexington; Amiram B. Ilan, Newton, both of Mass.

[73] Assignee: Prototech Company, Newton Highlands, Mass.

[21] Appl. No.: 673,041

[22] Filed: Nov. 19, 1984

[51] Int. Cl.$^4$ .................. H01M 4/86; C25B 11/03
[52] U.S. Cl. .................................. 204/265; 204/266; 204/283; 204/284; 429/42
[58] Field of Search ............... 204/265, 268, 270, 283, 204/284, 266; 429/42

[56] References Cited

U.S. PATENT DOCUMENTS 4,407,905  10/1983  Takeuchi ........................... 429/42

OTHER PUBLICATIONS

Sheibley et al, J. of Electrochem. Soc., vol. 130, No. 2, 1983, pp. 255-259.

Primary Examiner—John F. Niebling
Attorney, Agent, or Firm—Rines and Rines, Shapiro and Shapiro

[57] ABSTRACT

This invention is concerned with catalytic gas-diffusion structures such as electrodes and barriers comprising, as an integral part of a portion thereof, a non-ionic aqueous gel such as a polyvinyl alcohol, rendering said electrode impervious to gas percolation, while retaining electrolyte contact with the structures; and with methods of using said electrodes or barriers in a variety of electrochemical systems including electrolysis cells, fuel cells, batteries and others, as well as in metal-recovery systems involving no electricity.

15 Claims, 2 Drawing Figures

POLYMERIC HYDROGEL-CONTAINING GAS DIFFUSION ELECTRODES AND METHODS OF USING THE SAME IN ELECTROCHEMICAL SYSTEMS

The present invention relates to electrochemical systems employing an active gas such as hydrogen, oxygen (air) and the like, interacting with an electrolyte on a catalytic barrier and is directed to novel gas diffusion structures for use in such systems, particularly though not exclusively, to gas diffusion electrodes. The term "electrochemical system", as used herein, includes fuel cells, batteries and electrolysis cells for the production of electricity and/or chemicals under a D/C current, as well as non-current carrying systems comprising an aqueous electrolyte, a catalytic barrier and an active gas, said systems being useful in such diverse applications as the recovery of metals and the like ions in aqueous solutions, and the detection and electroanalysis of gaseous pollutants, such as carbon monoxide.

As is well know, catalytic gas-diffusion electrodes function usually in a three-phase environment consisting of a solid catalytic electrode, a preferably aqueous electrolyte solution and an active gas. Though no theoretical interpretation is needed as explanation of this invention, it is plausible to accept the common view that the contact point between the aqueous electrolyte and the active gas on the catalytic sites of the solid electrode is the seat of the electrochemical reaction, which involves electron release or capture at practically acceptable rates. In practice, in the fuel cell area, gas-diffusion electrodes are made by catalyzing and wet-proofng gas-porous structures such as porous carbon papers, carbon cloth, metal screen and the like, with an appropriate mixture, for example, of TEFLON and a platinum-on-carbon catalyst. Here the wet-proofing serves the purpose of preventing "flooding" of the pores of the electrode with an aqueous electrolyte solution, while retaining gaseous access to, and wetting of the catalyst sites. Experience has shown that electrode-flooding causes often disastrous slowdowns of the electrochemical reaction, because of interference with the gaseous diffusion to the electrode. It is usually necessary to prevent at least partial flooding of electrodes, by supplying the gas at a sufficient pressure, thereby causing gas percolation through the otherwise porous electrodes. Excessively pressurized gases, on the other hand, cause often serious drops in electrode performance by preventing adequate wetting of the electrode.

Generally, active gases such as hydrogen, oxygen (or even air, when it has to be freed from carbon dioxide for alkaline electrochemical systems), should not be allowed to percolate through the electrodes, as percolation causes not only a net loss of reagent but constitutes often a hazard and entails other disadvantages, later described herein.

An object of the present invention, accordingly, is to provide a novel improved catalytic gas-diffusion electrode or barrier structure that is not subject to the above-described percolation and other disadvantages, but that, to the contrary, enable greater efficiency and other improved operation. Another object is to provide a new and improved method of interacting a gas (such as hydrogen) at such catalytic electrode or barrier with an aqueous electrolyte (such as a metal ion-containing solution, for example, by a process described in U.S. Pat. No. 4,331,520 of common assignee, for the recovery of the metals). Yet another object is to provide electrochemical systems comprising such electrodes or barriers wherein active gases (such as hydrogen and oxygen) are prevented from intermingling.

Further objects are explained hereinafter and are particularly delineated in the appended claims.

In its broadest aspects, the present invention provides gas diffusion electrodes and like structures and electrochemical systems comprising the same, and method of using the same therein, said structures comprising, as an integral part of a portion thereof, a substantially non-ionic aqueous polymeric gel, said gel being capable of preventing gas percolation through said electrode and of restricting electrolyte access thereto to diffusional and electrochemical transport.

Figure 2:
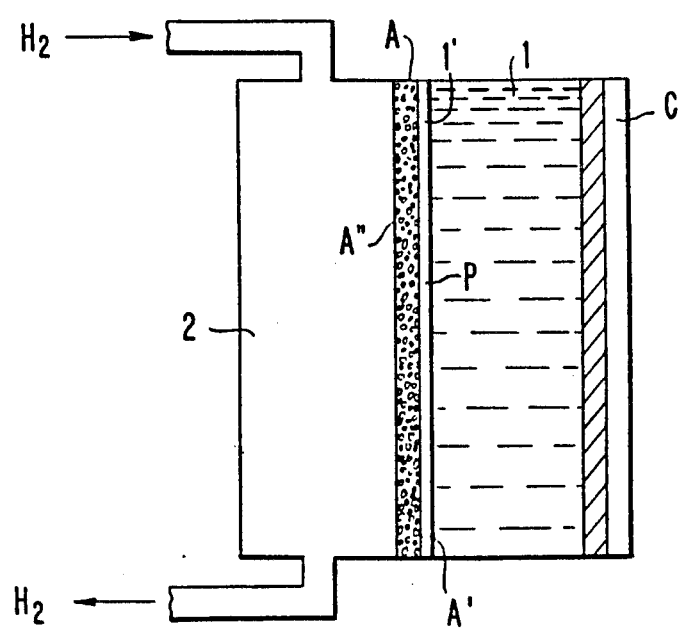

The invention will be further described in conjunction with the accompanied drawings, wherein:

FIG. 1 is a schematic view of the essential components of a gas impervious, but solution permeable, gas diffusion electrode; and FIG. 2 is a cross-sectional view of a preferred embodiment of the invention adapted for hydrogen depolarization anode operation and the like.

Turning first to the prior art, a typical non-ionic aqueous gel film, namely a cross-linked polyvinyl alcohol, (PVA) film, has been used as a battery separator, for example, in an alkaline silver-zinc battery. In accordance with the article entitled "Crosslinked Polyvinyl Alcohol Films as Alkaline Battery Separators" by Dean W. Sheibley et. al., Journal of the Electrochemical Society, Vol. 130, #2, (1983) pages 255ff, a cross-linked hydrated polyvinyl alcohol (PVA) separator, wrapped around the zinc electrodes, is evaluated as to its resistivity, dendrite penetration rate and zincate ion diffusivity. Evidently, in battery use there is no three-phase reaction present, the electrochemical reaction consisting in the solid zinc anode dissolving in the liquid electrolyte with release of electrons during discharge, and dissolved zinc ions being plated as solid zinc with capture of electrons during charge. Applying the PVA film directly to the zinc anode, instead of wrapping the zinc anode, (a possibility suggested in the article, as a potential cost lowering scheme) is merely another technique of wrapping. Such hypothetical directly applied film cannot remain an integral part of the zinc anode during its functioning as the zinc metal bearing the PVA film dissolves in the electrolyte, thereby inherently becoming detached from the solid film. Morover, any PVA film, to be useful in a battery, whether wrapped around or initially applied to the zinc (or other) electrode must cover the entire electrode to prevent dendritic shorts, that is it must not leave any of the electrode PVA-free.

Ion exchange membranes which are cross-linked aqueous polyelectrolyte gels, have been physically contacted with gas diffusion electrodes as, for example, shown in U.S. Pat. No. 3,124,520 by one of the applicants of the present invention. The electric resistivity of such ion exchange membrane gels is, generally, at least one order of magnitude greater than that of a corresponding electrolyte solution, i.e. liquid aqueous electrolyte of the same ionic concentration as the membrane. The reason for this inherently much larger resistivity is the lopsided ionic character of the crosslinked polyelectrolyte which has one mobile ion, whereas the other ion is immobile, being an ionic group chemically bonded to the polymeric structure. And the fixed ionic charge of such a membrane obviously bars substantially ions of the same sign to enter the aqueous gel, thereby limiting the diffusion of electrolyte into the membrane. There is thus a fundamental difference between such ionic polyelectrolyte gels and non-ionic aqueous gels such as the above named polyvinyl alcohol, which permits diffusion of mobile ions of both signs into the gel thus barely increasing the gel's electrolytic resistivity compared to that of the corresponding liquid electrolyte solution. Moreover, when the mobile counter ion of the polyelectrolyte's fixed ion is a polyvalent ion, such as, for example, the $Zn^{++}$ or the $Cu^{++}$ ion in the case of a sulfonic ion-exchange membrane, the resistivity of the zinc or copper sulfonate membrane is excessive to the point of being often entirely prohibitive.

The term non-ionic aqueous polymeric gel (also abbreviated to "hydrogel"), as used herein, refers to hydrated substantially water and/or liquid electrolyte-insoluble polymers, which are preferably, though not necessarily, crosslinked, said polymers being substantially free from ionizable groups chemically linked to said polymer. It is an essential characteristic of the non-ionic hydrogels of this invention that they are gas-impervious, while allowing electrolytes consisting of mobile ions of both signs, with and/or without associated water of hydration, to diffuse freely into the aqueous phase of the gel.

Referring now to FIG. 1, there is shown a schematic drawing of the essential components of the gas impervious, but solution penetrable, gas diffusion electrode and the like of this invention. A catalytic hydrophobic layer 2, is deposited on an electrically conducting fiber or the like support 1, said fibers, or wires, being for example, supplied in the form of a carbon paper or cloth or a metal screen, as is known in the fuel cell electrodes. FIG. 1 thus represents schematically a localized small area of a typical fuel cell electrode. The open pores, shown in magnified form in FIG. 1, of the normal fuel cell electrode, allow access of gas to the catalyst 2, provided they are not flooded with aqueous electrolyte: Such flooding must be minimized or prevented, for example, by supplying the gas under pressure. It is here that the detrimental percolation of the active gas occurs, in the absence of the non-ionic polymeric gel of this invention.

Further, flooding can occur not only because the liquid pressure exceeds the gaseous pressure, but also as a result of the water moved, for example as water of hydration, with dissolved ions under D.C. current.

When the open pores are blocked by anchoring the hydrogel, on the electrolyte-facing surface of the electrode, while retaining the remainder of the electrode accessible to the gas, diffusion and/or electrochemical transport of said ions from the liquid into the hydrogel occurs. In this fashion the necessary contact between the catalytic layer and the ions of the electrolyte is maintained by the solid gel coating while the gel-free gas side of the electrode insures gaseous access thereto. Alternately, the same result is attained when the hydrogel is anchored within the open pores and the gas is fed to the electrode by "edge feed", as shown in U.S. Pat. No. 4,478,696, of common assignee, incorporated herein by reference.

In practice we have found that anchoring of the hydrogel either on one side or within a gas diffusion electrode or barrier prevents gas percolation, allows the electrode or barrier to perform flawlessly, and affects diffusion and/or electrochemical electrolyte movement into and across the gel to the gas side sufficiently to prevent interference with the gaseous access.

Preferred and best embodiments hereinafter set forth illustrate the invention using polyvinyl alcohol and polyethylene oxide as typical examples of the non-ionic hydrogel. Suitable for the purpose of this invention in general, however, is the broad class of non-ionic hydrogels which includes gels comprising at least one polymer or co-polymer of a hydrophilic substantially non-ionic monomer. Typical monomers include glycol and glycerol, monoacrylates and monomethacrylates, propylene oxide, acrylamide and methacrylamide, and their like, in addition to the above named polymers from vinyl alcohol and ethylene oxide. Such gels of the prior art are generally described in U.S. Pat. Nos. 4,331,783 4,337,327 and 4,379,874 to V. A. Stoy, incorporated herein by reference. It is understood that the selection of a suitable hydrogel is made on the basis of combining an adequate water content of the gel with an adequate dimensional stability, which combination is readily determined experimentally in any particular electrolyte solution, by simply varying cross-linking agents, cross-linking levels and/or molecular weights of the polymer.

While the non-ionic hydrogel can convert any of the known porous gas diffusion electrodes, in the fuel cell and related arts, to the gas-impervious electrode of this invention, a preferred porous catalytic electrode or barrier structure to receive said hydrogels is the carbon cloth type electrode, comprising for example the platinum-on-carbon TEFLON layer and a particle platinum size range of 15–25 Å, as described in U.S. Pat. Nos. 4,044,193, 4,293,396 and 4,248,682 of common assignee, herein incorporated by reference, such as are specifically described in Example 1 of said U.S. Pat. No. 4,293,396.

In practice, the problem of gas percolation as well as excessive loss of liquid electrolyte is particularly serious, when large size electrodes are required which are extending into sizable depths of the order of several feet, into an electrolyte bath. Here the standard porous gas diffusion electrode cannot prevent serious gas percolation at the upper surface of the electrode, because excessive flooding occurs at the lower part due to the liquid electrolyte head. This becomes especially serious when the electrode is a hydrogen anode in an electrolytic cell, where the highly diffusible hydrogen percolates through the upper portion, constituting a significant economic loss, and where excessive flooding of electrolyte at the bottom causes unacceptable performance losses, due in part to significant current density variations over the anodic surface.

One specific application of the invention will now be described with reference to the accompanying drawing, FIG. 2, which is a cross-sectional view of a preferred embodiment of the invention adapted for hydrogen depolarization anode operation and the like. Referring to FIG. 2, the hydrogen anode A of an electrochemical cell as, for example, for the electrolytic recovery of zinc from an electrolyte solution 1 of zinc sulfate and sulfuric acid, said anode being of the platinum-catalyzed porous carbon cloth before described, and an aluminum (starting sheet) cathode C. Whereas, as before described, a porous catalyzed hydrogen anode A would normally dissipate or percolate hydrogen gas into the electrolyte, and electrolyte would normally leak excessively into the hydrogen feed chamber 2, these deleterious effects have been admirably overcome, in accordance with the invention, by coating the inner surface A' of the catalyzed carbon cloth anode A with a layer of polyvinyl alcohol (PVA) gel, cast as an intimate film P over the inner anode surface A', dried and then heat-treated to seal to the carbon cloth surface at A'. The PVA layer P is then permeated or filled with electrolyte, swelling to contain about fifty-percent of water, by weight of film; the electrolyte in the layer P (as shown at 1' in FIG. 2), now contacts the catalyst of the carbon cloth electrode at or near the section A', that is the electrode area which has been merged with the PVA gel. This provides an interface section within the electrode A for gas entering the left-hand surface A" to cause the effective catalytic conversion of hydrogen gas to hydrogen ion within the carbon cloth electrode adjacent the layer P, as fresh dissolved ions continually enter the PVA hydrogel layer P supplying the adjacent section A' of the anode therewith, thereby completing the three-phase environment required for efficient anodic hydrogen oxidation. The $H_2$ gas is stopped at the gas-impervious layer P and does not pass through into the electrolyte 1.

Here, these surprising properties and results are obtained with the novel, non-consumable (three phase) anode containing the permanently integrated hydrogel, and retaining a hydrogel-free portion for $H_2$-access in contrast to the above-referred to PVA battery-separator protecting the entire consumable, (two-phase) electrode from, for example, dendritic shorts.

EXAMPLE 1

As an example of coating one surface of a gas-diffusion electrode with a hydrogel, 50 grams of a high molecule weight PVA made and sold by the Dupont Company under the trade name ELVANOL 72-60 (described, for example, in Dupont Company's brochure entitled ELVANOL, Third Edition, 1961, incorporated herein by reference) was dissolved in one liter of distilled water containing also 1.0 grams of ammonium chloride, by boiling for several hours until substantially complete dissolution of the PVA. The solution was cooled to ambient temperature and a clear solution was obtained upon decantation from a small insoluble residue. The resulting approximately 5% PVA solution was stable, when stored in a location protected from light. The solution was then applied, by brushing, to one surface of the above-referred to electrode, of Example 1, U.S. Pat. No. 4,293,396, and the resulting film was dried at room temperature. Three coats were applied, each being dried for about one-half hour between applications. The coated electrode was then heated for about one-half hour at 125° C. to increase the film's insolubility, and cooled to ambient temperature. The coated electrode was then ready for use in an electrochemical system comprising an aqueous electrolyte solution, the PVA-coated surface to be contacted by the solution and the uncoated surface to be contacted by an active gas. The PVA-coated electrode tolerates continuous, for example, hydrogen pressure of up to 12" of water above the liquid electrolyte pressure without separation of the coating from the structure.

EXAMPLE 2

Stronger adherence of the PVA gel was attained, when the aqueous 5% PVA solution of Example 1 was diluted with isopropanol to the extent of 33% by volume of isopropanol contained solution, and applied to the electrode, as described in Example 1. The isopropanol causes the PVA to penetrate the electrode structure, resulting in strengthening the bond between the electrode and the PVA gel, allowing gas pressures of up to 40" of water to be used with no percolation and no PVA gel separation from the electrode. Here the hydrogel appears to have been anchored in its entirety within the electrode, with, however, exposed area available on the electrode's "backside" for gaseous access. There is no surface PVA film present on the "front side", as determined visually and by the fact that no PVA film can be lifted from the electrode under pressures in excess of 40" of water (which can cause some percolation).

Combined partial embedding with film coating was also obtained by using a 10% isopropanol solution, in lieu of the above 33.3% solution.

Finally, by using the above referred to "edge feed" technique such as described in Example 1 of the above referred to U.S. Pat. No. 4,478,696, a PVA-gel containing electrode was made covering both surfaces of the electrode, but allowing the PVA-free edge portion accessible to, for example, hydrogen gas.

EXAMPLE 3

As a first example of a successful test of the invention applied to the hydrogen anode-involving recovery of zinc from a before-mentioned $ZnSO_4$ aqueous electrolyte (100 grams $H_2SO_4$, 60 grams $ZnSO_4$), an anode 6×6 inches constructed of the before-described carbon cloth (on Stackpole Company's cloth labeled PWB 6), catalyzed by platinum particles in the previously mentioned 15–25 Å range distributed evenly over both surfaces of the cloth and in the interstices thereof in a TEFLON binder, and a 6×6 inch aluminum starting sheet cathode were employed. The thickness of the anode was about 15 mils and its platinum loading was 0.3 mg/cm$^2$.

The same cell without the use of the invention, operated with the electrodes at three-foot depths, was found to cause flooding of electrolyte in the bottom third thereof and into the hydrogen feed chamber, as well as substantial $H_2$ gas percolation into the upper third of the electrolyte chamber, requiring a cell voltage of about 2.56 volts at 90 amperes/square foot, and necessitating hydrogen back pressure of 36 inches to prevent substantially total flooding of the anode. With two coats of PVA, applied as a 4 mil thick film on the anode, as described in Example 1 above, the cell was operable at a $H_2$ back pressure of 38 inches without $H_2$-percolation, requiring the substantially smaller cell voltage of 1.88 volts, at 90 amperes/square foot, resulting in a thirty percent energy savings over operation without the invention (the cell voltage, under a given current, being directly proportional to the energy consumption of the cell).

In addition, the cathode zinc recovered at the aluminum cathode was remarkably uniform (30–33 mils near the top and 34–36 mils near the bottom after several hours of operation), as contrasted with the same-dimensioned cell without the PVA coating (14–16 mils near the bottom, and 28 mils near the top).

The following example illustrates the advantage of the hydrogel-containing structure, when used in the metal-recovery process of U.S. Pat. No. 4,331,520 with the gaseous supply means of U.S. Pat. No. 4,478,696, both patents having been incorporated herein by reference (and being of common assignee).

EXAMPLE 4

As described in Example 1, a 4 mil thick layer of the PVA solution was applied, by a doctor's blade, to one surface of the carbon cloth electrode. While the applied PVA film was still wet, the coated electrode was exposed to two doses, of 10 Megarads each, of γ-radiation from Cobalt-60 source. The resulting crosslinked polyvinyl alcohol gel film contained about 80% water, by weight of film, and was, preferably, kept wet to avoid the danger of embrittlement during drying. The coated anode was used as a hydrogen anode in the zinc-plating electrolysis cell as in Example 3 above, the anode having an active area of 2"×2". At 90 amperes per square foot a cell voltage of 1.67 was obtained.

This example illustrates the use of a cross-linked non-ionic hydrogel. The value of cross-linked film, versus, for example, the non-cross-linked film of Example 1, resides in the much lower water-solubility of the former. Evidently, other known techniques of cross-linking, utilizing, for example, known multifunctional chemical agents (such as di-aldehydes) may also be used.

EXAMPLE 5

Utilizing the Pt-catalyzed barrier of the "520" patent in the form of a strip (1" wide by 3" long) and the rim feed system of the "696" patent to deliver hydrogen gas to said barrier, copper "cementing" (i.e. copper recovery) tests were run in a four liter reservoir of magnetically stirred copper sulfate electrolyte solution containing 300 mg/l $Cu^{++}$. In a first test the barrier was run under ambient conditions, that is, with an air saturated electrolyte and no gel coating on the barrier, in a second test the barrier was coated with the above-described Dupont grade 72-60 PVA to between 1 and 2 grams/ft$^2$ of barrier are and operated with air saturated electrolyte. The results tabulated below clearly show the advantage of the PVA coating: Here, it is plausible to speculate that the PVA film substantially limits the access of oxygen to the barrier which would, in its absence, lead to a parasitic oxygen reduction on the barrier at the expense of copper cementation.

| Copper Depletion mg/l | Standard Barrier Cementation Rate mg Cu/min | PVA Coated Barrier Cementation Rate mg Cu/min |
|---|---|---|
| 300–100 | 1.856 | 3.836 |
| 300–50 | 1.485 | 2.928 |

The rate of recovering the dissolved copper (the "cementation rate") on the PVA-coated barrier was more than twice that of the "standard" barriers.

EXAMPLE 6

Another non-ionic polymeric organic hydrophobic gel-like coating of polyethylene oxide (type M.W. 100,000 Aldrich Chemicals) having somewhat similar, though less efficacious characteristics, has been used on the above platinum catalyzed carbon cloth hydrogen depolarization anode (having an active area of 2"×2") in a $ZnSO_4$ electrolyte zinc-recovery cell, at one-foot depth. A six percent water solution of the polyethylene oxide (molecular weight 100,000) was coated four times on the electrolyte side providing a coating that again prevented excessive flooding and H$_2$ percolation, but with somewhat lesser cell performance. Though this film did not result in energy conservation, it maintained hydrogen efficiency.

Other non-ionic polymeric thin films selected, for example, from the above-named hydrogels, strong enough to maintain integrity under pressures of at least 30–40 inches, but hydrophylic enough to allow aqueous electrolyte swelling therein, and being H$_2$-tight, may also be employed. As above stated, the techniques of the invention may also be applied to other catalyzed porous anode or other electrode materials and, of course, may be used in other metal-recovery cells as well as other types of electrochemical cells that can benefit from the results attainable with the invention.

Other advantages of hydrogel-containing electrodes include the following. As pointed out above, in an electrochemical cell comprising a gas diffusion electrode and a flowing electrolyte, it is not uncommon for the gas, especially if under any overpressure, to pass through the gas diffusion electrode and percolate into the electrolyte, often for as long as it takes to arrive at a delicate balance of the electrolyte and gas pressures under which gas percolation occurs. Such a condition is especially dangerous in a typical hydrogen-air fuel cell or, say, in a lithium-air aqueous battery, with narrow gaps between the anode and cathode, that is cells that have a limited escape path for the percolating gas and in which hydrogen and oxygen (air) could be mixed, as a result of percolation, producing a violent reaction due to the Pt-catalyst, when present. The hydrogel-containing electrodes, whether cross-linked or not, eliminate gas percolation even at very significant gas overpressures, thereby preventing the above dangerous condition. (Note that the Lithium anode in an aqueous battery always produces some parasitic hydrogen.)

Finally, in a hydrogen-oxygen (air) fuel cell, the reaction product is water which is produced at the anode in an alkaline cell and at the cathode in an acid cell. When water recovery is important, the hydrogel-containing electrodes permit substantial localization of the reaction water at one or the other electrode without cross-diffusion thereby facilitating water recovery.

Electrochemical techniques for monitoring toxic gas concentration, as well as oxygen deficiency, are commonly used. These voltametric sensors for toxic gases are selective, as for example for carbon monoxide in air. Such devices can employ a gas diffusion electrode in conjunction with an electrolyte, counter electrode and reference electrode. Again, the use of a PVA coating on the electrode eliminates any possibility of the gas in question to percolate into the electrolyte chamber which would disrupt the detector's balance.

Other uses and modifications will occur to those skilled in this art and such are considered to fall within the spirit and scope of the invention as defined in the appended claims.

What is claimed is:

1. A catalytic gas-diffusion structure comprising electrode for use in an electrolytic cell having, as an integral part of a portion thereof, a substantially non-ionic, aqueous, polymeric gel, said gel being capable of preventing gas-percolation through said electrode and of restricting electrolyte access thereto to diffusional and electrochemical transport, and other portions of the electrode providing access to gas flow.

2. The structure of claim 1, wherein the gel of said electrode comprises at least one of a polymer and copolymer of a hydrophobic substantially non-ionic monomer.

3. The structure of claim 2, wherein said monomer is selected from glycol and glycerol monoacrylates and monomethacrylates, vinyl alcohol, ethylene oxide, propylene oxide acrylamide and methylacrylamide and their N-substituted derivatives and glutarimide.

4. The structure of claim 2, wherein at least one polymer is cross-linked.

5. Ihe structure of claim 1, wherein the gel is a polyvinyl alcohol.

6. An electrochemical system having, in combination, an aqueous electrolyte solution containing an electrode having opposing surfaces, at least one of which is in contact with said solution and having as an integral part of said one surface, a substantially non-ionic, aqueous, polymeric gel capable of preventing gas-percolation and of restricting electrolyte access thereto to diffusional and electrochemical transport, such that diffused electrolyte is dissolved in said gel, and means for applying an electrochemically active gas in contact with one of the opposite surface and edges of the electrode separated from said electrolyte solution.

7. In a gas diffusion-electrode assembly, gas diffusion electrode means having opposing surfaces, at least one of which is to contact an electrolyte, said one surface only being coated with an aqueous gel of polyvinyl alcohol.

8. In an electrochemical system comprising an aqueous electrolyte, a gas-diffusion electrode having opposing surfaces at least one of which is in contact with said electrolyte, said electrode having an aqueous non-ionic gas-impervious organic polymeric hydrophobic gel bonded to said one surface as an integral part of said electrode.

9. A method of rendering a catalyzed electrode of porous material impervious to the percolation therethrough of gas applied to one porous surface thereof and of restricting access of electrolyte to the other surface to diffusional and electrochemical transport, that comprises, coating the said other surface of the catalyzed electrode with an aqueous polyvinyl alcohol gel and embedding said gel within said electrode and sealing the same thereto, contacting said gel-coated catalyzed surface with the electrolyte, and introducing gas at said one surface, thereby reacting the gas introduced at the said one surface with the electrolyte held diffused into said gel at said other surface of the catalyzed electrode.

10. A method as claimed in claim 9, and in which said electrode material comprises carbon cloth catalyzed with platinum particles and said gel is secured to, along and within the said other surface.

11. A method as claimed in claim 9, and in which said electrode is operated as an anode, said gas comprises hydrogen, and said electrolyte comprises an aqueous solution of ions of a metal that can be electroplated at a cathode.

12. In an electrolytic electrochemical cell employing a gas diffusion electrode, a method of restricting electrolyte access to and gas percolation through said electrode, that comprises, applying to one surface of the gas diffusion electrode an aqueous gel of polyvinyl alcohol and embedding the same therein while keeping the other surface gel-free, and disposing the electrode in the cell with said one surface contacting the electrolyte thereof.

13. The method of anchoring a non-ionic substantially water-insoluble hydrogel on a catalytic gas diffusion electrode and which comprises the steps of applying a solution of a hydrogel-forming compound consisting of one of a monomer and a soluble polymer to a portion only of said electrode and polymerizing said compound to a substantially water-insoluble gas-impermeable hydrogel.

14. The method of claim 13 wherein said solution comprises an aqueous isopropyl alcohol solution and wherein said compound is selected from vinyl alcohol and a soluble polyvinyl alcohol, thereby anchoring said hydrogel at least partly within the structure of said electrode.

15. The method of claim 14 wherein said compound is cross-linked by.

* * * * *